(12) United States Patent
Nita

(10) Patent No.: US 8,226,566 B2
(45) Date of Patent: Jul. 24, 2012

(54) DEVICE AND METHOD FOR VASCULAR RE-ENTRY

(75) Inventor: Henry Nita, Redwood Shores, CA (US)

(73) Assignee: FlowCardia, Inc., Sunnyvale, CA (US)

( * ) Notice: Subject to any disclaimer, the term of this patent is extended or adjusted under 35 U.S.C. 154(b) by 407 days.

(21) Appl. No.: 12/456,143

(22) Filed: Jun. 12, 2009

(65) Prior Publication Data

US 2010/0317973 A1 Dec. 16, 2010

(51) Int. Cl.
*A61B 8/14* (2006.01)
*A61B 17/20* (2006.01)
*A61M 5/178* (2006.01)
*A61H 1/00* (2006.01)

(52) U.S. Cl. ..... 600/466; 600/462; 604/22; 604/164.01; 601/2

(58) Field of Classification Search .................. 600/433, 600/437, 462, 466; 604/22, 164.01; 601/2
See application file for complete search history.

(56) References Cited

U.S. PATENT DOCUMENTS

| | | |
|---|---|---|
| 3,433,226 A | 3/1969 | Boyd |
| 3,565,062 A | 2/1971 | Kuris |
| 3,631,848 A | 1/1972 | Muller |
| 3,719,737 A | 3/1973 | Vaillancourt et al. |
| 3,823,717 A | 7/1974 | Pohlman et al. |
| 3,896,811 A | 7/1975 | Storz |
| 4,016,882 A | 4/1977 | Broadwin et al. |
| 4,033,331 A | 7/1977 | Guss et al. |
| 4,136,700 A | 1/1979 | Broadwin et al. |
| 4,337,090 A | 6/1982 | Harrison |
| 4,368,410 A | 1/1983 | Hance |
| 4,417,578 A | 11/1983 | Banko |
| 4,425,115 A | 1/1984 | Wuchinich |
| 4,486,680 A | 12/1984 | Bonnet et al. |
| 4,505,767 A | 3/1985 | Quin |
| 4,565,589 A | 1/1986 | Harrison |
| 4,572,184 A | 2/1986 | Stohl et al. |
| 4,664,112 A | 5/1987 | Kensey et al. |
| 4,665,906 A | 5/1987 | Jervis |
| 4,679,558 A | 7/1987 | Kensey et al. |
| 4,700,705 A | 10/1987 | Kensey et al. |
| 4,721,117 A | 1/1988 | Mar et al. |
| 4,750,902 A | 6/1988 | Wuchinich et al. |
| 4,808,153 A | 2/1989 | Parisi |
| 4,811,743 A | 3/1989 | Stevens |
| 4,827,911 A | 5/1989 | Broadwin et al. |
| 4,838,853 A | 6/1989 | Parisi |
| 4,854,325 A | 8/1989 | Stevens |
| 4,870,953 A | 10/1989 | DonMicheal et al. |
| 4,886,060 A | 12/1989 | Wiksell |
| 4,920,954 A | 5/1990 | Alliger et al. |
| 4,923,462 A | 5/1990 | Stevens |

(Continued)

FOREIGN PATENT DOCUMENTS

DE 2256127 5/1974

(Continued)

*Primary Examiner* — Michael Rozanski
(74) *Attorney, Agent, or Firm* — Knobbe Martens Olson & Bear, LLC

(57) ABSTRACT

In a method for re-entry from extraluminal space into the central lumen of a vessel, a guidewire is advanced into the extraluminal space of the vessel, and then a directional catheter is advanced over the guidewire through the extraluminal space. Thereafter, the guidewire is removed from the directional catheter, an ultrasound device is placed through the directional catheter, and the ultrasound device is advanced through the extraluminal space into the central lumen and then activated.

24 Claims, 7 Drawing Sheets

U.S. PATENT DOCUMENTS

| | | |
|---|---|---|
| 4,924,863 A | 5/1990 | Sterzer |
| 4,931,047 A | 6/1990 | Broadwin et al. |
| 4,936,281 A | 6/1990 | Stasz |
| 4,936,845 A | 6/1990 | Stevens |
| 5,000,185 A | 3/1991 | Yock |
| 5,015,227 A | 5/1991 | Broadwin et al. |
| 5,026,384 A | 6/1991 | Farr et al. |
| 5,046,503 A | 9/1991 | Schneiderman |
| 5,053,008 A | 10/1991 | Bajaj |
| 5,058,570 A | 10/1991 | Idemoto et al. |
| 5,076,276 A | 12/1991 | Sakurai |
| 5,091,205 A | 2/1992 | Fan |
| 5,100,423 A | 3/1992 | Fearnot |
| 5,114,414 A | 5/1992 | Buchbinder |
| 5,116,350 A | 5/1992 | Stevens |
| 5,127,917 A | 7/1992 | Niederhauser et al. |
| 5,156,143 A | 10/1992 | Bocquet et al. |
| 5,163,421 A | 11/1992 | Bernstein et al. |
| 5,180,363 A | 1/1993 | Idemoto et al. |
| 5,195,955 A | 3/1993 | Don Michael |
| 5,215,614 A | 6/1993 | Wijkamp et al. |
| 5,221,255 A | 6/1993 | Mahurkar et al. |
| 5,226,421 A | 7/1993 | Frisbie et al. |
| 5,234,416 A | 8/1993 | Macaulay et al. |
| 5,238,004 A | 8/1993 | Sahatjian et al. |
| 5,242,385 A | 9/1993 | Strukel |
| 5,243,997 A | 9/1993 | Uflacker et al. |
| 5,248,296 A | 9/1993 | Alliger |
| 5,255,669 A | 10/1993 | Kubota et al. |
| 5,267,954 A | 12/1993 | Nita |
| 5,269,291 A | 12/1993 | Carter |
| 5,269,297 A | 12/1993 | Weng et al. |
| 5,269,793 A | 12/1993 | Simpson |
| 5,287,858 A | 2/1994 | Hammerslag et al. |
| 5,290,229 A | 3/1994 | Paskar |
| 5,304,115 A | 4/1994 | Pflueger |
| 5,304,131 A | 4/1994 | Paskar |
| 5,312,328 A | 5/1994 | Nita et al. |
| 5,324,255 A | 6/1994 | Passafaro et al. |
| 5,324,260 A | 6/1994 | O'neill et al. |
| 5,325,860 A | 7/1994 | Seward et al. |
| 5,326,342 A | 7/1994 | Pflueger et al. |
| 5,341,818 A | 8/1994 | Abrams et al. |
| 5,342,292 A | 8/1994 | Nita et al. |
| 5,344,395 A | 9/1994 | Whalen et al. |
| 5,346,502 A | 9/1994 | Estabrook et al. |
| 5,362,309 A | 11/1994 | Carter |
| 5,368,557 A | 11/1994 | Nita |
| 5,368,558 A | 11/1994 | Nita |
| 5,378,234 A | 1/1995 | Hammerslag et al. |
| 5,380,274 A | 1/1995 | Nita |
| 5,380,316 A | 1/1995 | Aita et al. |
| 5,382,228 A | 1/1995 | Nita et al. |
| 5,383,460 A | 1/1995 | Jang et al. |
| 5,389,096 A | 2/1995 | Aita et al. |
| 5,397,293 A | 3/1995 | Alliger et al. |
| 5,397,301 A | 3/1995 | Pflueger et al. |
| 5,405,318 A | 4/1995 | Nita |
| 5,409,483 A | 4/1995 | Campbell et al. |
| 5,417,703 A | 5/1995 | Brown et al. |
| 5,427,118 A | 6/1995 | Nita |
| 5,431,168 A | 7/1995 | Webster, Jr. |
| 5,431,663 A | 7/1995 | Carter |
| 5,443,078 A | 8/1995 | Uflacker |
| 5,447,509 A | 9/1995 | Mills et al. |
| 5,449,369 A | 9/1995 | Imran |
| 5,451,209 A | 9/1995 | Ainsworth et al. |
| 5,465,733 A | 11/1995 | Hinohara et al. |
| 5,480,379 A | 1/1996 | La Rosa |
| 5,484,398 A | 1/1996 | Stoddard |
| 5,487,757 A | 1/1996 | Truckai et al. |
| 5,507,738 A | 4/1996 | Ciervo |
| 5,516,043 A | 5/1996 | Manna et al. |
| 5,527,273 A | 6/1996 | Manna et al. |
| 5,540,656 A | 7/1996 | Pflueger et al. |
| 5,542,917 A | 8/1996 | Nita et al. |
| 5,597,882 A | 1/1997 | Schiller et al. |
| 5,607,421 A | 3/1997 | Jeevanandam et al. |
| 5,611,807 A | 3/1997 | O'Boyle |
| 5,618,266 A | 4/1997 | Liprie |
| 5,626,593 A | 5/1997 | Imran |
| 5,658,282 A | 8/1997 | Daw et al. |
| 5,695,460 A | 12/1997 | Siegel et al. |
| 5,695,507 A | 12/1997 | Auth et al. |
| 5,715,825 A | 2/1998 | Crowley |
| 5,720,724 A | 2/1998 | Ressemann et al. |
| 5,728,062 A | 3/1998 | Brisken |
| 5,738,100 A | 4/1998 | Yagami et al. |
| 5,797,876 A | 8/1998 | Spears et al. |
| 5,816,923 A | 10/1998 | Milo et al. |
| 5,827,203 A | 10/1998 | Nita |
| 5,830,222 A | 11/1998 | Makower |
| 5,895,397 A | 4/1999 | Jang et al. |
| 5,902,287 A | 5/1999 | Martin |
| 5,935,142 A | 8/1999 | Hood |
| 5,944,737 A | 8/1999 | Tsonton et al. |
| 5,957,882 A | 9/1999 | Nita et al. |
| 5,957,899 A | 9/1999 | Spears et al. |
| 5,964,223 A | 10/1999 | Baran |
| 5,967,984 A | 10/1999 | Chu et al. |
| 5,971,949 A | 10/1999 | Levin et al. |
| 5,976,119 A | 11/1999 | Spears et al. |
| 5,989,208 A | 11/1999 | Nita |
| 5,997,497 A | 12/1999 | Nita et al. |
| 6,004,280 A | 12/1999 | Buck et al. |
| 6,007,499 A | 12/1999 | Martin et al. |
| 6,007,514 A | 12/1999 | Nita |
| 6,030,357 A | 2/2000 | Daoud et al. |
| 6,051,010 A | 4/2000 | DiMatteo et al. |
| 6,113,558 A | 9/2000 | Rosenschein et al. |
| 6,123,698 A | 9/2000 | Spears et al. |
| 6,149,596 A | 11/2000 | Bancroft |
| 6,165,127 A | 12/2000 | Crowley |
| 6,165,188 A | 12/2000 | Saadat et al. |
| 6,179,809 B1 | 1/2001 | Khairkhahan et al. |
| 6,190,353 B1 | 2/2001 | Makower et al. |
| 6,206,842 B1 | 3/2001 | Tu et al. |
| 6,210,356 B1 | 4/2001 | Anderson et al. |
| 6,217,543 B1 | 4/2001 | Anis et al. |
| 6,231,546 B1 | 5/2001 | Milo et al. |
| 6,231,587 B1 | 5/2001 | Makower |
| 6,235,007 B1 | 5/2001 | Divino, Jr. et al. |
| 6,241,692 B1 | 6/2001 | Tu et al. |
| 6,241,703 B1 | 6/2001 | Levin et al. |
| 6,277,084 B1 | 8/2001 | Abele et al. |
| 6,283,983 B1 | 9/2001 | Makower et al. |
| 6,287,271 B1 | 9/2001 | Dubrul et al. |
| 6,287,285 B1 | 9/2001 | Michal et al. |
| 6,287,317 B1 | 9/2001 | Makower et al. |
| 6,296,620 B1 | 10/2001 | Gesswein et al. |
| 6,302,875 B1 | 10/2001 | Makower et al. |
| 6,315,741 B1 | 11/2001 | Martin et al. |
| 6,379,378 B1 | 4/2002 | Werneth et al. |
| 6,387,109 B1 | 5/2002 | Davison et al. |
| 6,394,956 B1 | 5/2002 | Chandrasekaran et al. |
| 6,398,736 B1 | 6/2002 | Seward |
| 6,416,533 B1 | 7/2002 | Gobin et al. |
| 6,423,026 B1 | 7/2002 | Gesswein et al. |
| 6,433,464 B2 | 8/2002 | Jones |
| 6,450,975 B1 | 9/2002 | Brennan et al. |
| 6,454,757 B1 | 9/2002 | Nita et al. |
| 6,454,997 B1 | 9/2002 | Divino, Jr. et al. |
| 6,491,707 B2 | 12/2002 | Makower et al. |
| 6,494,891 B1 | 12/2002 | Cornish et al. |
| 6,508,781 B1 | 1/2003 | Brennan et al. |
| 6,508,784 B1 | 1/2003 | Shu |
| 6,511,458 B2 | 1/2003 | Milo et al. |
| 6,524,251 B2 | 2/2003 | Rabiner et al. |
| 6,544,215 B1 | 4/2003 | Bencini et al. |
| 6,547,754 B1 | 4/2003 | Evans et al. |
| 6,551,337 B1 | 4/2003 | Rabiner et al. |
| 6,554,846 B2 | 4/2003 | Hamilton et al. |
| 6,558,502 B2 | 5/2003 | Divino, Jr. et al. |
| 6,562,031 B2 | 5/2003 | Chandrasekaran et al. |
| 6,589,253 B1 | 7/2003 | Cornish et al. |
| 6,596,235 B2 | 7/2003 | Divino, Jr. et al. |
| 6,623,448 B2 | 9/2003 | Slater |

| | | |
|---|---|---|
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner et al. |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,750 B2 | 3/2004 | Yock |
| 6,719,725 B2 | 4/2004 | Milo et al. |
| 6,733,451 B2 | 5/2004 | Rabiner et al. |
| 6,761,698 B2 | 7/2004 | Shibata et al. |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 7,004,173 B2 | 2/2006 | Sparks et al. |
| 7,056,294 B2 | 6/2006 | Khairkhahan et al. |
| 7,131,983 B2 | 11/2006 | Murakami |
| 7,137,963 B2 | 11/2006 | Nita et al. |
| 7,220,233 B2 | 5/2007 | Nita et al. |
| 7,267,650 B2 | 9/2007 | Chow et al. |
| 7,335,180 B2 | 2/2008 | Nita et al. |
| 7,384,407 B2 | 6/2008 | Rodriguez et al. |
| 7,425,198 B2 | 9/2008 | Moehring et al. |
| 7,494,468 B2 | 2/2009 | Rabiner et al. |
| 7,503,895 B2 | 3/2009 | Rabiner et al. |
| 7,540,852 B2 | 6/2009 | Nita et al. |
| 7,604,608 B2 | 10/2009 | Nita et al. |
| 7,621,929 B2 | 11/2009 | Nita et al. |
| 7,771,358 B2 | 8/2010 | Moehring et al. |
| 2003/0009153 A1 | 1/2003 | Brisken et al. |
| 2003/0036705 A1 | 2/2003 | Hare et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2005/0215946 A1 | 9/2005 | Hansmann et al. |
| 2005/0228286 A1 | 10/2005 | Messerly et al. |
| 2006/0206039 A1 | 9/2006 | Wilson et al. |
| 2006/0264809 A1 | 11/2006 | Hansmann et al. |
| 2007/0260172 A1 | 11/2007 | Nita |
| 2008/0108937 A1 | 5/2008 | Nita |
| 2008/0221506 A1 | 9/2008 | Rodriguez et al. |
| 2008/0228111 A1 | 9/2008 | Nita |
| 2008/0287804 A1 | 11/2008 | Nita |
| 2011/0130834 A1 | 6/2011 | Wilson et al. |

FOREIGN PATENT DOCUMENTS

| | | |
|---|---|---|
| DE | 2438648 | 2/1976 |
| DE | 3821836 | 1/1990 |
| DE | 4042435 | 8/1991 |
| EP | 0005719 | 12/1979 |
| EP | 0316789 | 5/1989 |
| EP | 0376562 | 7/1990 |
| EP | 0379156 | 7/1990 |
| EP | 0394583 | 10/1990 |
| EP | 0443256 | 8/1991 |
| EP | 0541249 | 5/1993 |
| EP | 0820728 | 1/1998 |
| GB | 1106957 | 3/1968 |
| JP | 01099547 | 4/1989 |
| JP | U03067608 | 7/1991 |
| JP | 2006086822 | 3/1994 |
| JP | 2007116260 | 5/1995 |
| JP | 10216140 | 8/1998 |
| JP | 2001104356 | 4/2001 |
| JP | 2001321388 | 11/2001 |
| JP | 2002186627 | 7/2002 |
| WO | WO8906515 | 7/1989 |
| WO | WO9001300 | 2/1990 |
| WO | WO9004362 | 5/1990 |
| WO | WO9107917 | 6/1991 |
| WO | WO9211815 | 7/1992 |
| WO | WO9308750 | 5/1993 |
| WO | WO9316646 | 9/1993 |
| WO | WO9412140 | 6/1994 |
| WO | WO9414382 | 7/1994 |
| WO | WO9508954 | 4/1995 |
| WO | WO9509571 | 4/1995 |
| WO | WO9635469 | 11/1996 |
| WO | WO9745078 | 12/1997 |
| WO | WO9925412 | 5/1999 |
| WO | WO0053341 A1 | 9/2000 |
| WO | WO00/67830 | 11/2000 |
| WO | WO2004012609 | 2/2004 |
| WO | WO2004112888 | 12/2004 |

DEVICE AND METHOD FOR VASCULAR RE-ENTRY

BACKGROUND OF THE INVENTION

1. Field of the Invention

The present invention pertains to medical devices and methods, and more particularly, to a method and catheter system for accessing the central lumen of a blood vessel from extraluminal space.

2. Description of the Prior Art

There have been many procedures and systems for treating vascular or venous obstructions that are occluded with atheroma, plaque or calcific material, and are often referred to as vascular chronic total occlusion. In the past, such cardiovascular diseases were treated using a dramatic and painful surgical bypass procedure. However, a recent development of catheter-based interventions is less traumatic, and shows better success rates and long term patency.

The catheter-based interventional procedures require that a guidewire is positioned through such an occlusion in a distal central lumen. In many instances, guidewire placement in the central distal lumen is difficult or almost impossible, mostly due to hard occlusive material or the inability to define a vessel path. Often, during such procedures, a guidewire deflects from the occlusion and penetrates into an extraluminal space (i.e., subintimal or outside the vessel). Frequently, a guidewire might perforate a vessel and end up outside of the vessel. While such perforations are very dangerous in certain circulations (e.g., in the brain and the heart), such perforations are less risky in peripheral arterial circulations and in most of the venous system due to the muscular tissue surrounding these areas.

Once in an extraluminal space, between layers of the vessel, it is difficult or often impossible to re-enter a guidewire into the central lumen even with the use of ancillary deflecting catheters or devices. In such cases, a catheter-based intervention cannot be performed and patient well being relies on more complex and painful surgical intervention.

SUMMARY OF THE DISCLOSURE

It is an object of the present invention to provide an improved method for facilitating re-entry from extraluminal space into the central lumen of a vessel.

In order to accomplish the objects of the present invention, there is provided a method for re-entry from extraluminal space into the central lumen of a vessel. According to this method, a guidewire is advanced into the extraluminal space of the vessel, and then a directional catheter is advanced over the guidewire through the extraluminal space. Thereafter, the guidewire is removed from the directional catheter, an ultrasound device is placed through the directional catheter, and the ultrasound device is advanced from the extraluminal space into the central lumen and then activated.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

Figure 1:
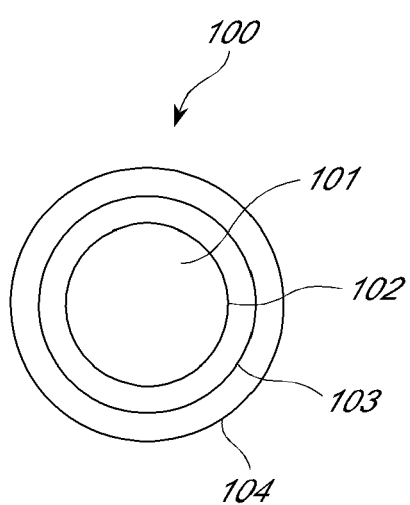
FIG. 1 is a cross-sectional view of a human artery.

A blood vessel is an elastic tubular channel, such as an artery, a vein, or a capillary, through which blood circulates. Arteries transport oxygenated blood away from the heart with one exemption of the pulmonary artery. FIG. 1 illustrates a normal healthy artery 100 having a central lumen 101 and arterial wall with three layers: intima 102, intermedia 103 and adventitia 104. All three layers consist of elastic tissue, smooth muscle and connecting tissue (collagen). The tissue of the arterial wall is often called a sub-intimal space. The area outside the adventitia 104, an external layer of the artery, is called a space outside of the vessel. Both areas, sub-intimal space and outside the vessel space, are referred to collectively herein as "extraluminal space".

Figure 2:
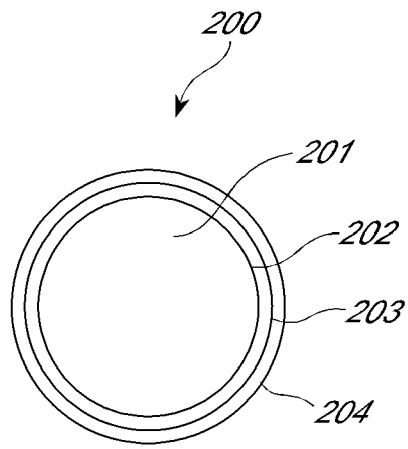
FIG. 2 is a cross-sectional view of a human vein.

Veins transport de-oxygenated blood towards the heart with one exemption of the pulmonary vein. FIG. 2 illustrates a normal healthy vein 200 having a central lumen 201 and arterial wall with three layers as well: intima 202, intermedia 203 and adventitia 204. All three layers are identical to the layers of the arterial wall and also consist of elastic tissue, smooth muscle and connecting tissue (collagen). The walls of the veins are thinner and less elastic than the corresponding layers of arteries, and transport blood at lower pressure than arteries. Veins include valves that aid the return of blood to the heart by preventing blood from running in the reverse direction. The tissue of the vein wall is also called a sub-intimal space. The area outside the adventitia, an external layer of the vein, is also called a space outside of the vessel. Both areas, sub-intimal space and outside the vessel space, are referred to collectively herein as "extraluminal space".

Figure 3:
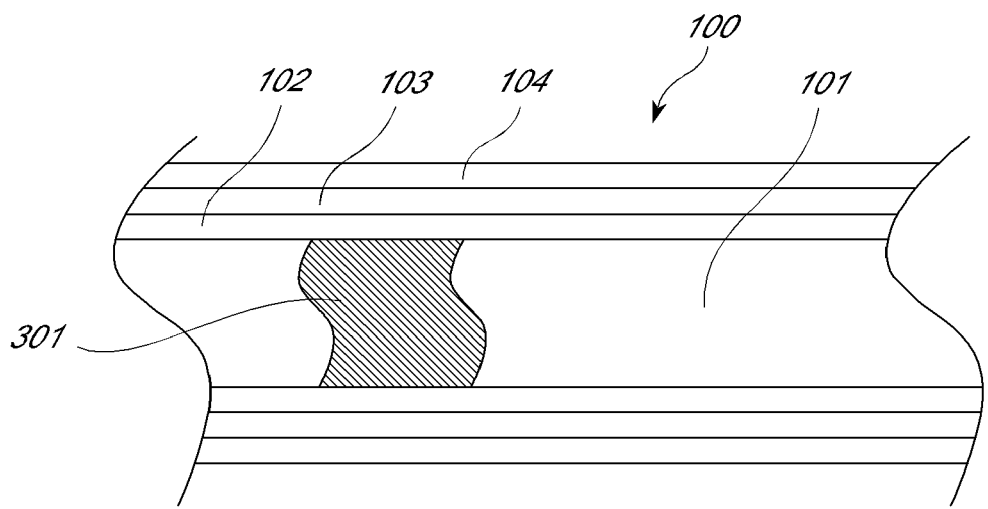
FIG. 3 illustrates an artery or vein that has total occlusion.

A Total Occlusion (TO) is defined as an artery or vein that has been completely occluded. Acute Total Occlusions usually are associated with a sudden blockage and no blood flow to and from surrounding tissue, and are potentially life threatening. In contrast, Chronic Total Occlusions (CTO) are those that have formed for at least thirty days and are less life-threatening. In such cases, the areas around CTOs tend to develop collateral blood supply. FIG. 3 illustrates a total occlusion 301 that usually consists of atheroma, thrombus, plaque, calcific material or combinations of all of these materials. For illustrative purposes, an Arterial Chronic Total Occlusion 301 will be shown in connection with the method of FIGS. 3-11. However, all the methods described herein can also apply to chronic total occlusions within veins. Such Chronic Total Occlusion occupies the entire lumen, thus blocking blood flow. It has been proven by several scientific publications that it is desirable to open such Chronic Total Occlusions and restore blood flow through affected areas to improve blood supply and heart Left Ventricular Function. Examples of such publications include:

Immediate Results and One-Year Clinical Outcome After Percutaneous Coronary Interventions in Chronic Total Occlusions; Z. Olivari, P. Rubartelli, F. Piscione, F. Ettori, A. Fontanelli, L. Salemme, C. Giachero, C. Di Mario, G. Gabrielli, L. Spedicato, F. Bedogni on behalf of the TOAST-GISE Investigators; JACC, May 2003; Vol 41 No 10: 1672-1678

Outcome of PTCA and Stenting in Diabetic and Nondiabetic Patients: A Report from the Total Occlusion Study of Canada (TOSCA) Investigators; V. Dzavik, K. Yee, T. Anderson, E. Cohen, J. Mancini, D. Catellier, G. Barbeau, J. Ducas, C. Lazzam, J. Burton, P. Berger, C. Buller; JACC, March 2002: p. 28A Procedural Outcomes and Long-Term Survival Among Patients Undergoing Percutaneous Coronary Intervention of a Chronic Total Occlusion in Native Coronary Arteries: A 20-Year Experience; J. Suero, S. Marso, P. Jones, S. Laster, K. Huber, L. Giorgi, W. Johnson, B. Rutherford; JACC, August 2001; Vol 38 No 2: 409-414.

According to the present invention, methods and devices are provided to facilitate re-entry of interventional devices, such as guidewires or catheters, from an extraluminal space (or outside of the vessel) into the central lumen of the vessel. If the chronic total occlusion is longer, such a re-entry can take place at any location along the occlusion. The re-entry can also be made into the existing occlusion or distally beyond the occlusion.

Referring to FIGS. 4-11, in one embodiment, a guidewire 401 is passed in an extraluminal space and its distal end is positioned beyond the CTO 301, or at a desirable location for re-entry into the distal central lumen 101D. An access catheter or a deflecting catheter 501 is placed over this guidewire 401 either in a rapid exchange or over-the-wire fashion at the vicinity of the distal end of the guidewire 401. The access catheter 501 is bent or curved at its distal end, and can be manipulated and directed toward the distal central lumen 101D. To facilitate the correct positioning of the access catheter 501, a series of radiopaque markers 503 may be situated on the distal end of the catheter 501, or the distal end of the catheter 501 may be made of a radiopaque polymer. The access catheter 501 may have a pre-shaped distal end 502 and should exhibit an excellent torque response characteristic and visibility under fluoroscopy to further facilitate directional movements. Once the access catheter 501 is positioned at the re-entry area, the guidewire 401 is removed, and the access catheter 501 remains in the subintimal space or outside the vessel.

An ultrasound or vibrational device 701 is then introduced through the access catheter 501 and positioned distally. When it is confirmed (under fluoroscopy) that the distal end of the access catheter 501 is directed towards the distal central lumen 101D, the ultrasound device 701 is activated and slowly advanced through the subintimal space to puncture the vessel wall. After the ultrasound device 701 reaches the distal central lumen 101D, ultrasound energy activation stops and the ultrasound device 701 is positioned further distally in the distal central lumen 101D. The distal end of the access catheter 501 is advanced through the created re-entry pathway over the ultrasound device 701 into central lumen 101. Subsequently, the ultrasound device 701 is removed from the access catheter 501 and any guidewire 401 of choice (or another catheter) may be positioned in the distal central lumen 101D via the access catheter. Thereafter, the access catheter 501 is removed from the body, and with any conventional guidewire 401 located in the distal central lumen 101D, the patient is ready for a diagnostic or interventional procedure.

In another embodiment, devices utilizing different sources of energy or forces may be used to re-enter the distal central lumen 101D from the subintimal space, including but not limited to: vibrational devices, rotational device, cutting devices, radiofrequency devices, laser devices, microwave devices and puncture devices.

In yet another embodiment of the present invention, in addition to fluoroscopic imaging, an intravascular ultrasound or other imaging modalities may be employed, including Optical Coherence Tomography (OCT) or magnetic fields (Stereotaxis Inc.) to further facilitate orientation of the access catheter 501 towards the distal central lumen 101D and help in the re-entry procedure.

The apparatus of the present invention comprises an ultrasound system that includes an ultrasound device 701 and an access catheter 501. Such a deflecting or directing catheter 501 has a catheter body having a proximal end, at least one lumen extending therethrough, and a distal end 502 that has a pre-formed bend or curve. The same deflecting function may be achieved with a catheter having an actuated distal end, as is well-known in the art. Such a bend should be suitable to deflect the distal end of the ultrasound device 701. The deflecting catheter 501 should have good torque response and good distal bend/shape retention. Both characteristics are important for positioning and manipulation of the deflecting catheter 501 while selecting directions toward the distal central lumen 101D. Both characteristics may be achieved using shapeable polymers (with or without metal or polymer reinforcement systems) that are well-known in the art. The shape and the length of shaped distal end of such a deflecting catheter 501 may vary in length between 1 mm-20 mm and in angle between 5-90°. The ultrasound or vibrational device 701 of the present invention may be an ultrasound or vibrational catheter, guidewire or a simple cannula, and may operate at frequencies between 10 Hz and 20 MHZ in continuous mode, pulse mode or combination of both. Several examples of such devices are shown and described in U.S. Pat. Nos. 4,870,953; 4,920,954; 5,267,954; 5,304,115; 5,427,118; 5,989,208; 6,007,514; 7,137,963; 7,220,293; 7,297,131; 7,335,180; 7,393,338; 7,540,852 and in Pub. Nos. 20080108937 and 20080287804. The ultrasound device 701 can be provided with a self deflecting capability, as a catheter with an actuating distal end. Such a device may be used for re-entry from an extraluminal space without the use of a deflecting catheter 501. If a guidewire ends up in extraluminal space, the ultrasound device with a deflecting/actuated tip is introduced distally in the subintimal space, and then deflected accordingly, activated and advanced toward the distal central lumen 101D. Alternatively, a pre-shaped ultrasound device may be used to re-enter from an extraluminal space without use of a redirecting catheter.

Figure 4:
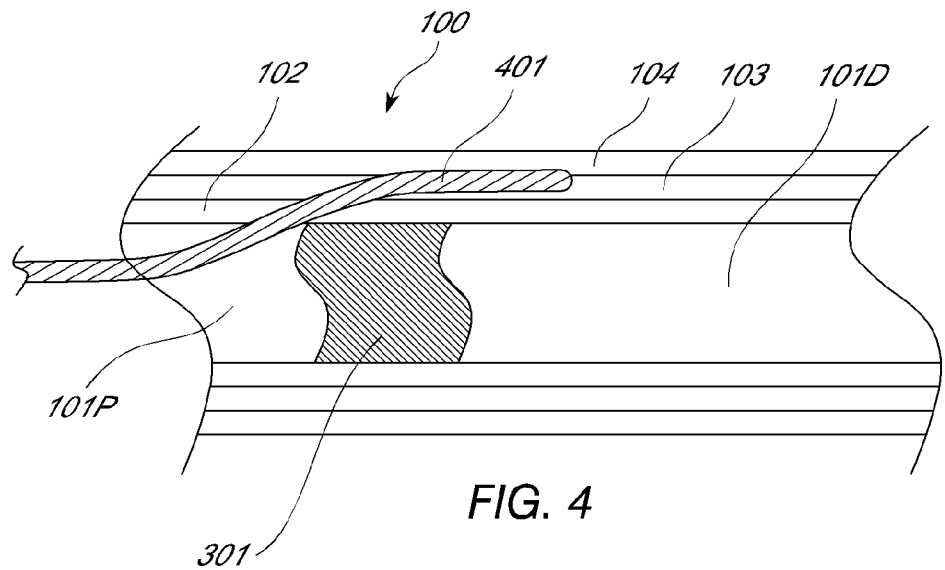
FIGS. 4-11 illustrate a method according to the present invention for re-entry from extraluminal space into the central lumen using an ultrasound device according to the present invention.

Referring now to FIG. 4, a guidewire 401 according to the present invention is advanced in a vessel until it faces the CTO 301. Sometimes, the guidewire 401 can be successfully advanced through the CTO 301 and positioned in the distal central lumen 101D of the vessel 100. Once the guidewire 401 is in the central proximal lumen 101P, and beyond the CTO 301, an adjunctive angioplasty such as balloon angioplasty and/or stenting can follow to complete an interventional procedure. However, as shown in FIG. 4, the guidewire 401 often deflects from the CTO 301 and penetrates the vessel wall 100. The guidewire 401 in FIG. 4 is shown to have penetrated the intima layer 102, and ending up between the intermedia 103 and adventitia 104 layers. The guidewire 401 can be advanced within the vascular layers until it passes the CTO 301. It can also be easily advanced more distally within the subintimal space. However, it is desirable that advancement of the guidewire 401 within the subintimal space be as short as possible, just beyond the proximal end of the CTO 301. Often, when CTOs 301 are long and there is evidence of softer occlusion composition, the proximal advancement of the guidewire 401 should be limited as much as possible. If possible, re-entry within the CTO 301 should be considered as well to minimize the length of the subintimal space which the guidewire 401 will occupy. Re-entry of the guidewire 401 from the subintimal space into the central distal lumen 101D may encounter serious difficulties, or the guidewire 401 may be unable to re-enter into the central proximal lumen 101P, due to the muscular vessel structure. In such cases, either a guidewire is too soft to puncture the vessel wall, or the directing catheter provides insufficient support, or both.

Figure 5:
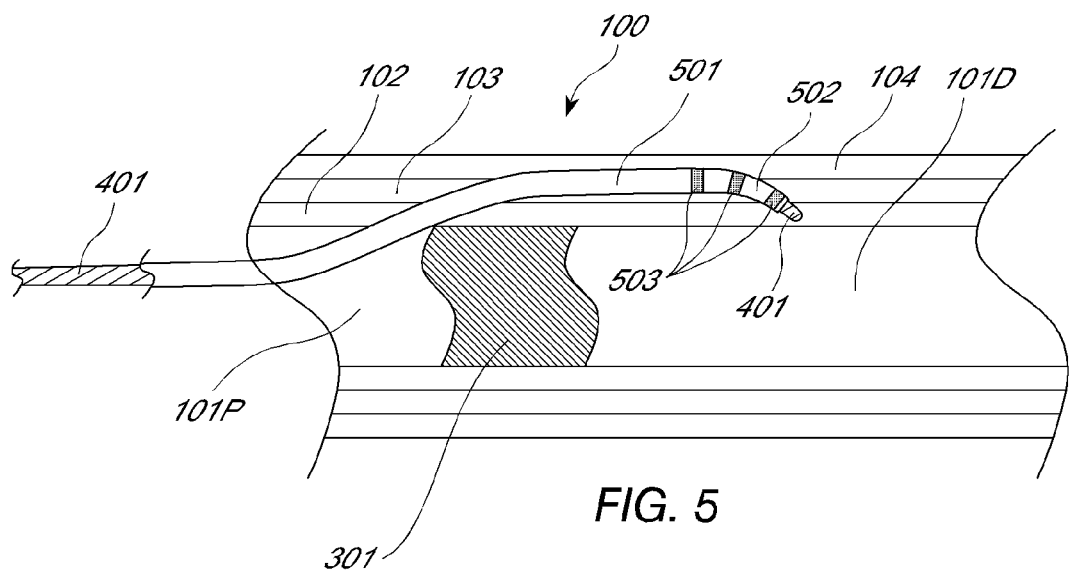

FIG. 5 shows a deflection catheter 501 having a shaped distal end 502 that is introduced over the guidewire 401 in the subintimal space between media 103 and adventitia 104. To provide better visibility, such a deflecting catheter 501 may be provided with radiopaque markers 503 or can be made of a radiopaque material for better visibility under fluoroscopy. The deflecting catheter 501 serves to direct the guidewire 401 into the distal central lumen 101D. The guidewire 401 and the deflecting catheter 501 may be advanced and manipulated in parallel or sequentially until the guidewire 401 is positioned in a direction that faces the central distal lumen 101D. Next, the guidewire 401 is removed.

Figure 6:
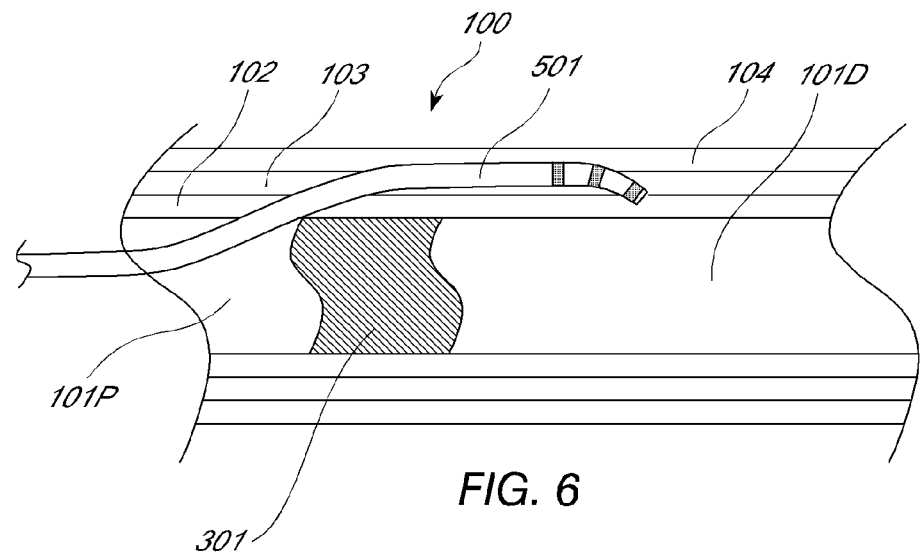

FIG. 6 shows the deflecting catheter 501 still positioned within the subintimal space between the media layer 103 and adventitia layer 104, after the guidewire 401 has been removed.

Figure 7:
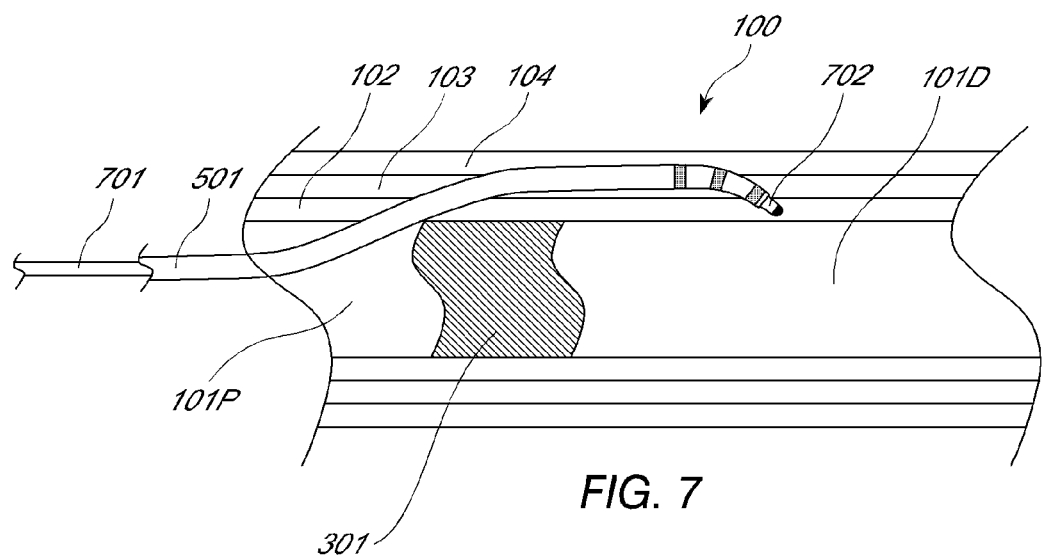

In the next step, an ultrasound device 701 is introduced. FIG. 7 illustrates the defecting catheter 501 in the subintimal space, and with the ultrasound device 701 (having a distal end 702) positioned through the deflecting catheter 501. Ultrasonic energy with its cavitational and/or thermal effect(s) may be very helpful in ablating or penetrating, perforating or piercing the vessel wall 100, and then facilitating re-entry into the central distal lumen 101D. Also, vibrational devices with longitudinal or transverse vibrational forces, rotational devices or other heat generating devices such as radiofrequency or microwave devices may also be used to facilitate re-entry into the central distal lumen 101D. The ultrasound device 701 may be activated and then advanced through deflecting catheter 501 into the central distal lumen 101D.

Figure 8:
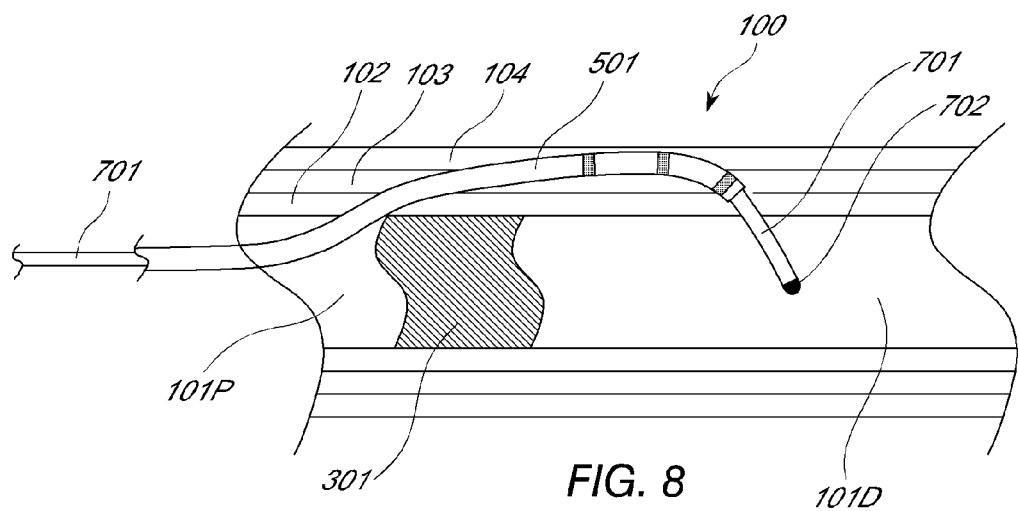

Then, as shown in FIG. 8, the ultrasound device 701 is advanced into the distal central lumen 101D and positioned beyond the CTO 301.

Figure 9:
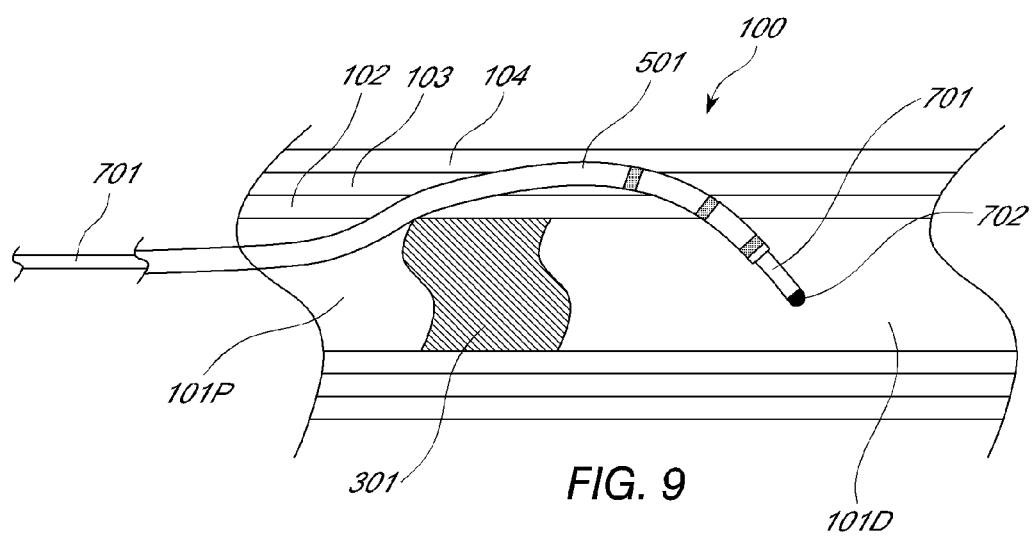

Next, as shown in FIG. 9, the deflecting catheter 501 is advanced over the ultrasound device 701 from the subintimal space of the vessel wall into the distal central lumen 101D to a location beyond the CTO 301.

Figure 10:
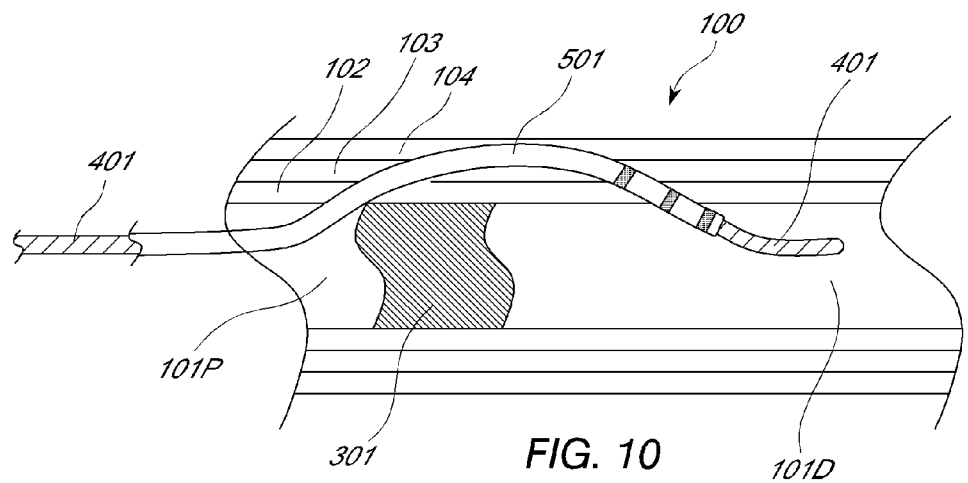

FIG. 10 illustrates the deflecting catheter 501 positioned around the CTO 301 through the subintimal space and into the distal central lumen 101D. The ultrasound catheter 701 is removed and replaced by the guidewire 401 which has been inserted through the deflecting catheter 501 until its distal end is positioned in the distal central lumen 101D.

Figure 11:
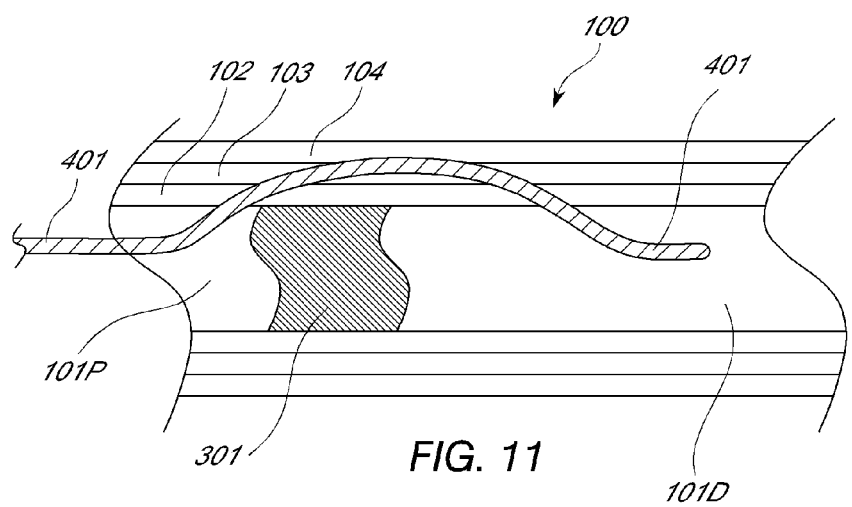
Figure 12:
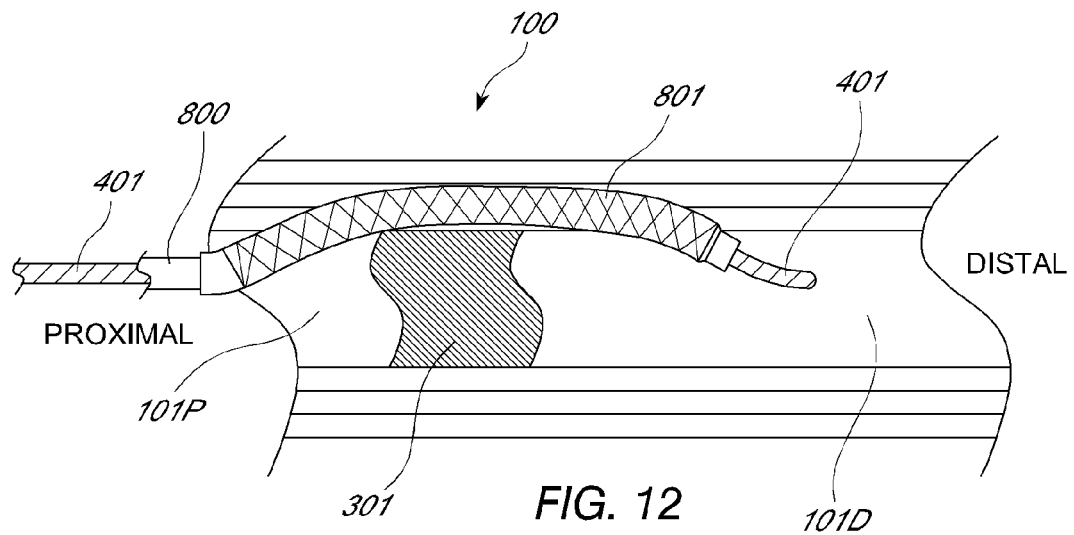
FIGS. 12-13 illustrate a follow-up stent placement after the steps illustrated in FIGS. 4-11.
Figure 13:
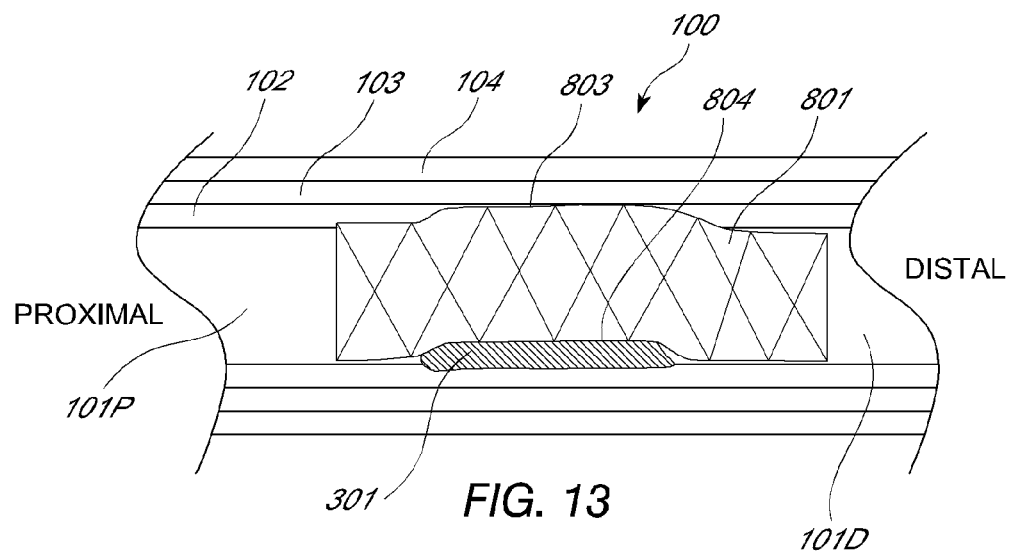

Next, the deflecting catheter 501 is removed. FIG. 11 illustrates the guidewire 401 positioned through the subintimal space of the vessel 100 into the central distal lumen 101D, after the deflecting catheter 501 has been removed. Such a guidewire position is required to continue an interventional angioplasty, either a balloon and/or stent procedure. An example of a stent procedure is illustrated in FIGS. 12-13 below. For example, FIG. 12 illustrates the guidewire 401 extended from the proximal part of the vessel 100, through the subintimal space and into the distal central lumen 101D of the vessel 100. A balloon catheter 800 with a stent 801 carried thereon is delivered over the guidewire 401 and positioned such that the distal part of the balloon 800 and the stent 801 are located in the distal central lumen 101D, and the proximal part of the balloon 800 and the stent 801 are located in the proximal central lumen 101P. As shown in FIG. 12, the balloon 800 and the stent 801 extend across the entire length of the CTO 301. The stent 801 is then deployed, and FIG. 13 shows the fully deployed stent 801 in the central lumen 101. The upper part 803 of the stent 801 penetrates the vessel wall into the subintimal space, while the lower part 804 of the stent 801 flattens and covers the CTO 301. With the stent 801 deployed in the central lumen 101, blood flow through the vessel 100 is restored.

In cases when the length of a CTO 310 is longer, such a re-entry procedure may be performed at any suitable location, even within the CTO 301, and not necessarily distally beyond the CTO 301.

In order to optimize the methods described above, an extensive flouroscopical visualization from several X-ray machine angles may be required. Such visualization is needed during positioning of the deflecting catheter 501 to assure that its distal end 502 is directed towards the central distal lumen 101D. Use of endovascular ultrasound or other visualization devices, either in arteries or in adjacent veins, may also help to facilitate directing of the deflecting catheter 501 towards the distal central lumen 101D.

Figure 14:
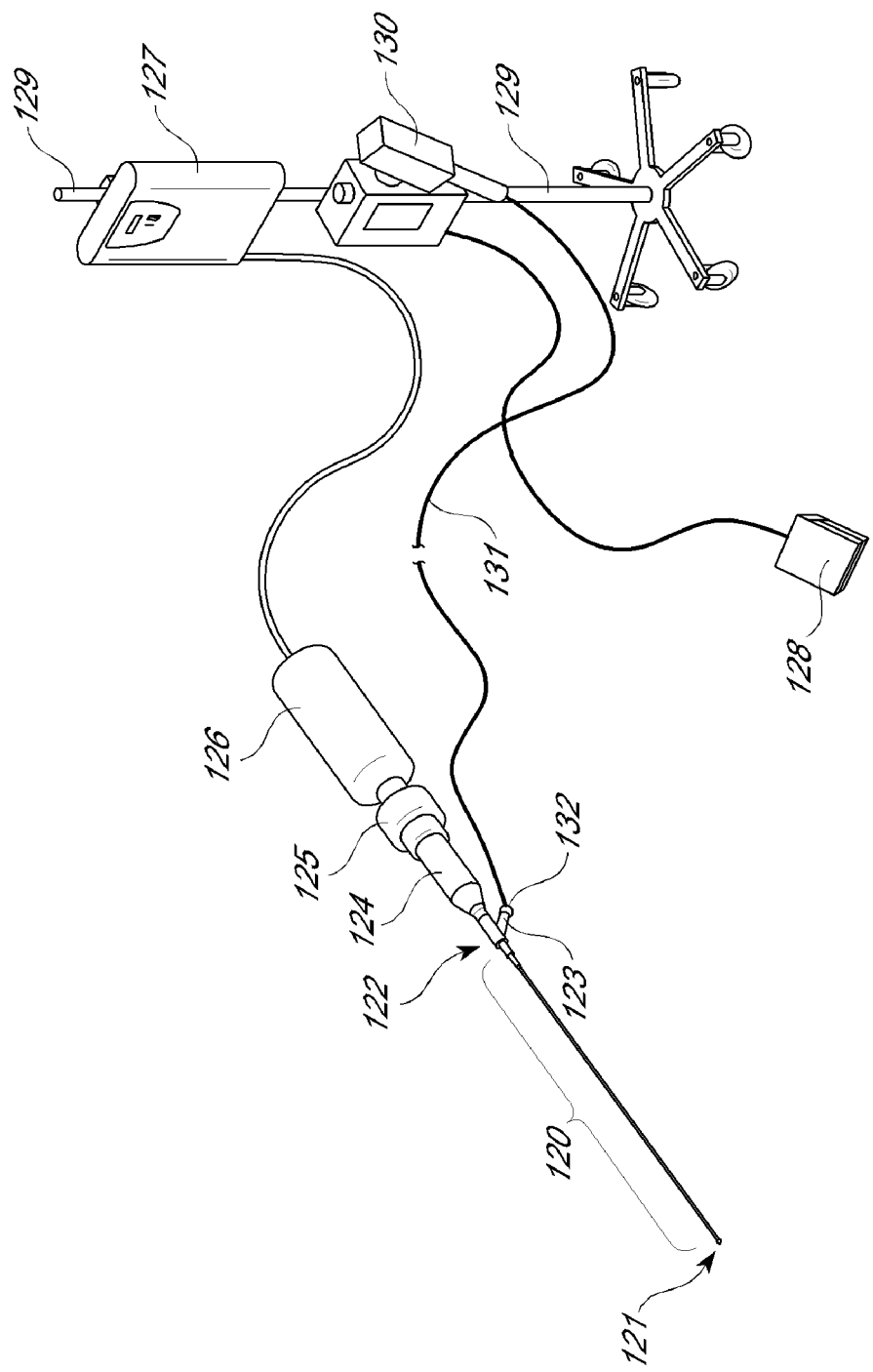
FIG. 14 is a perspective view of an ultrasound system that can be used to carry out the method illustrated in FIGS. 4-13.

FIG. 14 illustrates an example of an ultrasound system according to the present invention that can be used for re-entry into the central lumen 101 of a vessel 100. The ultrasound system includes an ultrasound device 120 which has an elongate body having a proximal end 122 and a distal end 121. Even though the numeral designation 120 is used in FIG. 14, it can be the same as the ultrasound device 700 described herein. The ultrasound device 120 can be an ultrasonic energy delivery member, or a catheter having at least one lumen extending longitudinally with an ultrasound transmission member extending therethrough. The ultrasound device 120 having the proximal end 122 and Y-connector 123 is operatively coupled by way of a device knob 124, and a slide collar 125 to the ultrasound transducer 126. The ultrasound transducer 126 is connected to a signal generator 127, which can be provided with a foot actuated on-off switch 128. The signal generator 127 can be supported by an IV pole 129. When the on-off switch 128 is depressed, the signal generator 127 sends an electrical signal to the ultrasound transducer 126, which converts the electrical signal to ultrasound energy. Such ultrasound energy subsequently passes through the catheter device 120 and is delivered to the distal end 121. A conventional guidewire may be utilized in conjunction with the device 120 (not shown).

The ultrasound device 120 may be a catheter formed of a flexible polymeric material such as nylon (Pebax) manufactured by Atochimie, Cour be Voie, Hauts Ve-Sine, France. The flexible catheter body is preferably in the form of an elongate tube having one or more lumens extending longitudinally therethrough. The catheter body defines a main lumen (not shown). Extending longitudinally through the main lumen is an elongate ultrasound transmission member (not shown) having a proximal end which is removably connectable to the ultrasound transducer 126 via a sonic connector (not shown) such that ultrasound energy will pass through the ultrasound transmission member. As such, when the foot actuated on-off switch 128 operatively connected to the ultrasound transducer 126 is depressed; ultrasound energy will pass through the ultrasound transmission member to the distal end 121 of the ultrasound device 120.

In one embodiment, the ultrasound transmission member may be formed of any material capable of effectively transmitting the ultrasonic energy from the ultrasound transducer 126 to the distal end 121 of the ultrasound device 120, and is preferably made from metal or metal alloys. It is possible to form all or a portion of the ultrasound transmission member with one or more materials which exhibit super-elasticity. Such materials should preferably exhibit super-elasticity consistently within the range of temperatures normally encountered by the ultrasound transmission member during operation of the ultrasound device 120. Specifically, all or part of the ultrasound transmission member may be formed of one or more metal alloys known as "shape memory alloys".

Examples of super-elastic metal alloys which are usable to form the ultrasound transmission member of the present invention are described in detail in U.S. Pat. Nos. 4,665,906 (Jervis); 4,565,589 (Harrison); 4,505,767 (Quin); and 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries, and behavior of specific metal alloys which are super-elastic within the temperature range at which the ultrasound transmission member of the present invention operates, any and all of which super-elastic metal alloys may be usable to form the super-elastic ultrasound transmission member.

The frontal portion of the Y-connector 123 is connected to the proximal end 122 of the ultrasound device 120 using techniques that are well-known in the art. An injection pump 130 or IV bag (not shown) or syringe (not shown) can be connected, by way of an infusion tube 131, to an infusion port or sidearm 132 of the Y-connector 123. The injection pump can be used to infuse coolant fluid into and/or through the device 120. Such flow of coolant fluid may be utilized to prevent overheating of the ultrasound transmission member and serves to bathe the outer surface of the ultrasound transmission member, thereby providing for an equilibration of temperature between the coolant fluid and the ultrasound transmission member. The temperature and/or flow rate of coolant fluid may be adjusted to provide adequate cooling and/or other temperature control of the ultrasound transmission member. The irrigation fluid can include a pharmacological agent and/or microbubbles.

In addition to the foregoing, the injection pump 130 or syringe may be utilized to infuse a radiographic contrast medium into the catheter 120 for purposes of imaging. Examples of iodinated radiographic contrast media which may be selectively infused into the catheter 120 via the injection pump 130 are commercially available as Angiovist 370 from Berlex Labs, Wayne, N.J. and Hexabrix from Malinkrodt, St. Louis, Mo.

The distal end 121 of the ultrasound device 120 may have a separate distal tip positioned on the ultrasound transmission member, as illustrated in U.S. Pat. No. 7,137,963 (FIG. 2). Alternatively, the distal end 121 of the ultrasound device 120 may be the end of the ultrasound transmission member, as illustrated in U.S. Pat. No. 5,304,115 (FIG. 14). Also, the ultrasound device 120 may itself be a guidewire that is energized by ultrasound energy, as illustrated in U.S. Pat. No. 5,427,118. The proximal end of the ultrasound transmission member is attached to a sonic connector (not shown), which is configured to effect operative and removable attachment of the proximal end of the ultrasound transmission member to the horn of the ultrasound transducer 126. The sonic connector is preferably configured and constructed to permit passage of ultrasound energy through the ultrasound transmission member with minimal lateral side-to-side movement of the ultrasound transmission member while, at the same time, permitting unrestricted longitudinal forward/backward vibration or movement of the ultrasound transmission member. Examples of ultrasound systems that include ultrasound transmission members (and their distal tips), ultrasound transducers, sonic connectors and their connections that can be used with the ultrasound device 120 are illustrated in U.S. Pat. Nos. 6,427,118; 6,702,748; 6,855,123; 6,942,620; 6,942,677; 7,137,963; 7,220,293; 7,297,131; 7,335,180; 7,393,338; 7,540,852 and in Pub. Nos. 20080108937 and 20080287804 whose disclosures are incorporated by this reference as though set forth fully herein.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method for re-entry from extraluminal space into the central lumen of a vessel, comprising:
   advancing a guidewire into the extraluminal space of the vessel;
   advancing a directional catheter over the guidewire through the extraluminal space;
   removing the guidewire from the directional catheter;
   placing an ultrasound device through the directional catheter;
   advancing the ultrasound device through the extraluminal space;
   activating the ultrasound device to penetrate the vessel and re-enter the central lumen;
   advancing the directional catheter into the central lumen so that a distal end of the directional catheter is distal to an occlusion;
   removing the ultrasound device; and
   advancing the guidewire through the directional catheter into the central lumen.

2. The method of claim 1, further including providing the directional catheter with a pre-shaped distal end.

3. The method of claim 1, further including providing the directional catheter with a side exit.

4. The method of claim 1, further including providing the directional catheter with a deflectable distal tip.

5. The method of claim 1, wherein the ultrasound device is an ultrasound wire.

6. The method of claim 1, wherein the ultrasound device is an ultrasound catheter.

7. The method of claim 1, further including operating the ultrasound device in one of the following mode of operation: continuous, pulse or combination of both.

8. The method of claim 1, further including operating the ultrasound device at frequencies between 17 KHz-20 MHz.

9. The method of claim 1, wherein the ultrasound device operates over a guidewire.

10. The method of claim 1, further including advancing the ultrasound device through the extraluminal space into the central lumen so that the distal end of the ultrasound device is distal of a chronic total occlusion.

11. The method of claim 1, further including: providing a radiopaque feature on the distal end of the directional catheter.

12. The method of claim 1, further including (i) removing the directional catheter, (ii) advancing a catheter over the guidewire, and (iii) performing a therapeutic procedure using the catheter.

13. The method of claim 1, further including (i) removing the directional catheter, (ii) advancing a catheter over the guidewire, and (iii) performing a diagnostic procedure using the catheter.

14. A method for re-entry from extraluminal space into the central lumen of a vessel, comprising:
- advancing a guidewire into the extraluminal space of the vessel;
- advancing a directional catheter over the guidewire through the extraluminal space;
- removing the guidewire from the directional catheter;
- placing a vibrational device through the directional catheter;
- advancing the vibrational device through the extraluminal space;
- activating the vibrational device to penetrate the vessel and re-enter the central lumen;
- advancing the directional catheter into the central lumen so that a distal end of the directional catheter is distal to an occlusion;
- removing the vibrational device; and
- advancing the guidewire through the directional catheter into the central lumen.

15. The method of claim 14, further including operating the vibrational device at frequencies between 10 Hz and 20 MHz.

16. A method for re-entry from extraluminal space into the central lumen of a vessel, comprising:
- positioning a directional catheter in the extraluminal space;
- advancing an ultrasound device;
- activating the ultrasound device to penetrate the vessel and re-enter the central lumen;
- advancing the directional catheter into the central lumen so that a distal end of the directional catheter is distal to an occlusion;
- removing the ultrasound device; and
- advancing a guidewire through the directional catheter into the central lumen.

17. The method of claim 16, further including positioning the ultrasound device through the directional catheter.

18. The method of claim 16, further including introducing the ultrasound device into the extraluminal space over the guidewire.

19. The method of claim 16, further including providing the ultrasound device with a deflectable distal end.

20. A method for re-entry from extraluminal space into the central lumen of a vessel, comprising:
- positioning an energy-based device in the extraluminal space;
- activating and advancing the energy-based device through the extraluminal space into the central lumen;
- advancing a directional catheter into the central lumen so that a distal end of the directional catheter is distal to an occlusion;
- removing the energy-based device from the directional catheter; and
- advancing a guidewire through the directional catheter into the central lumen.

21. The method of claim 20, wherein the energy-based device is an ultrasound device.

22. The method of claim 21, further including providing the ultrasound device with a deflectable distal end.

23. The method of claim 21, wherein the ultrasound device is operated over a guidewire.

24. The method of claim 20, wherein the energy based device comprises one of the following: ultrasound, vibrational, rotational, radiofrequency, microwave or laser energy.

* * * * *